(12) United States Patent
Streitmann et al.

(10) Patent No.: US 9,649,414 B2
(45) Date of Patent: May 16, 2017

(54) COLLECTION MEMBER FOR A NASAL ASPIRATOR AND NASAL ASPIRATOR

(71) Applicant: ATTRACT KFT., Pecs (HU)

(72) Inventors: Valter Streitmann, Pecs (HU); Zsolt Matraberci, Pecs (HU)

(73) Assignee: Attract Kft., Pecs (HU)

( * ) Notice: Subject to any disclaimer, the term of this patent is extended or adjusted under 35 U.S.C. 154(b) by 0 days.

(21) Appl. No.: 14/765,371

(22) PCT Filed: Mar. 4, 2013

(86) PCT No.: PCT/HU2013/000024
§ 371 (c)(1),
(2) Date: Aug. 3, 2015

(87) PCT Pub. No.: WO2014/135904
PCT Pub. Date: Sep. 12, 2014

(65) Prior Publication Data
US 2015/0367044 A1 Dec. 24, 2015

(51) Int. Cl.
*A61M 1/00* (2006.01)

(52) U.S. Cl.
CPC ........ *A61M 1/0009* (2013.01); *A61M 1/0023* (2013.01); *A61M 1/0039* (2013.01); *A61M 1/0086* (2014.02); *A61M 2205/071* (2013.01); *A61M 2205/076* (2013.01); *A61M 2210/0618* (2013.01)

(58) Field of Classification Search
CPC .... A61M 1/00; A61M 1/0001; A61M 1/0049; A61M 1/0056; A61M 1/0058; A61M 1/0062; A61M 2005/076; A61M 2205/082; A61M 2210/0618; A61M 1/0086; A61M 1/0009; A61M 1/0023; A61M 1/0039
USPC .................................. 604/28, 35, 118, 540
See application file for complete search history.

(56) References Cited

U.S. PATENT DOCUMENTS 5,800,425 A * 9/1998 DeLeonardis ...... A61M 1/0023
600/573

FOREIGN PATENT DOCUMENTS

FR 2 919 807 A1 * 2/2009 .......... A61M 1/0001

* cited by examiner

*Primary Examiner* — Philip R Wiest
(74) *Attorney, Agent, or Firm* — Olson & Cepuritis, Ltd.

(57) ABSTRACT

The invention relates to a collection member (10) for a nasal aspirator (100), the collection member (10) having a shell (12) defining a cavity (14), which shell (12) is provided with a nasal insertion end (16) and a hose connection end (18), characterised by comprising: —a first tubular element (20) protruding from the nasal insertion end (16) into the cavity (14) such that a first inner end (21) of the first tubular element (20) is located in the cavity (14), and —a second tubular element (22) protruding from the hose connection end (18) into the cavity (14) such that a second inner end (23) of the second tubular element (22) is located in the cavity (14), and a collar (24) is provided around the second tubular element (22), and the first and second tubular elements (20, 22) are arranged such that the collar (24) is interposed between the first inner end (21) and the second inner end (23). The invention further relates to a nasal aspirator (100) comprising such a collection member (10).

17 Claims, 2 Drawing Sheets

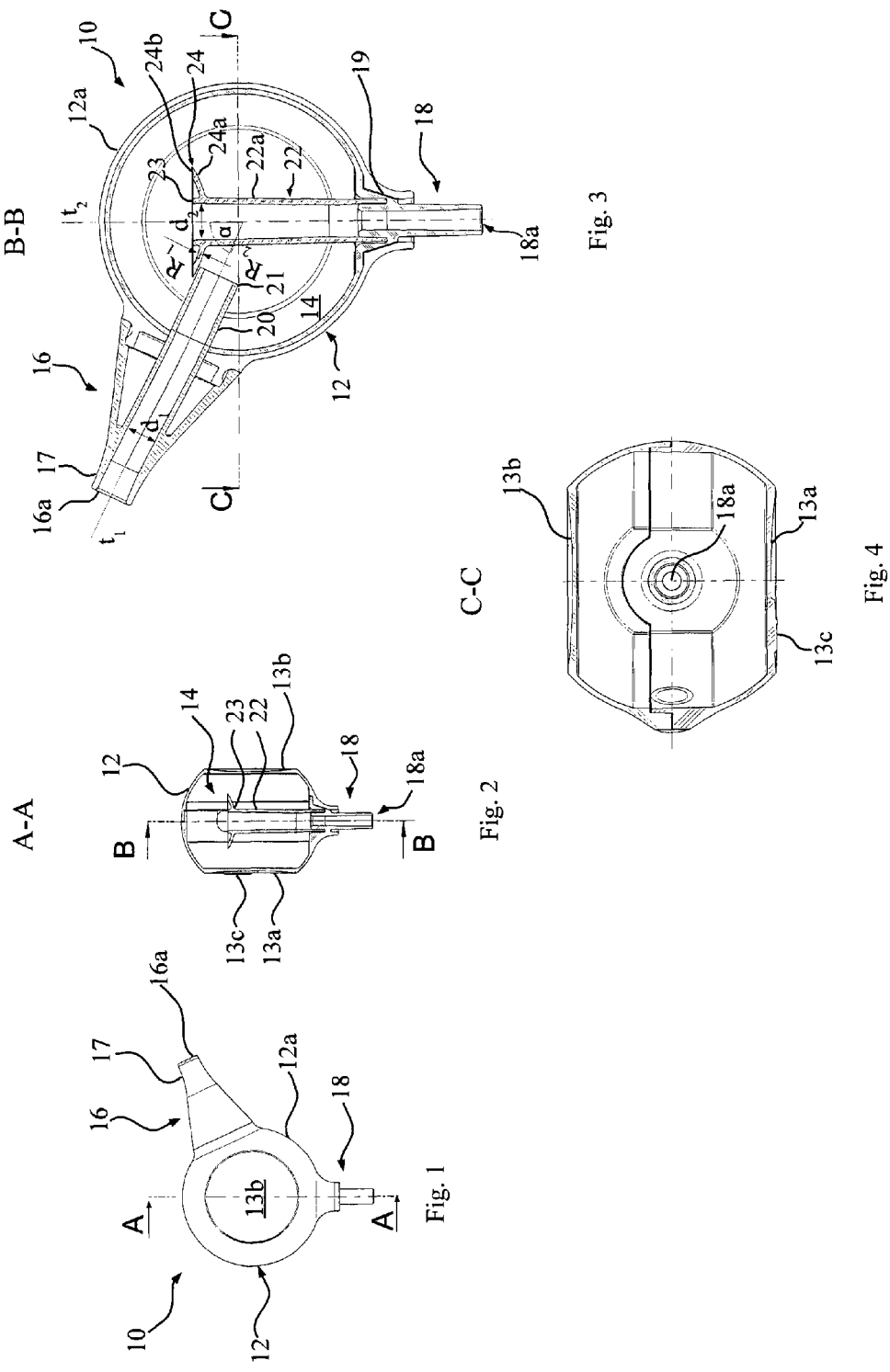

COLLECTION MEMBER FOR A NASAL ASPIRATOR AND NASAL ASPIRATOR

CROSS-REFERENCE TO RELATED APPLICATION

This application is a U.S. National Phase of PCT/HU2013/000024, filed Mar. 4, 2013, which is incorporated herein by reference.

The present invention relates to a collection member for a nasal aspirator, the collection member has a shell defining an inner cavity, which is provided with a nasal insertion end and a hose connection end.

The invention further relates to a nasal aspirator comprising such a collection member.

Nasal aspirators are commonly used for cleaning the nasal passages of young children. The accumulation of mucus in the nasal passages can be caused by infection but also by natural mucus production, hence nasal aspirators are indispensable for the nasal hygiene of healthy children as well.

Prior art nasal aspirators comprise a collection member for collecting mucus drawn from the nasal passages. U.S. Pat. No. 6,290,667 discloses a collection member that is formed as a bulb syringe: by squeezing the rubber wall of the bulb syringe air is evacuated from its hollow cavity, which creates a partial vacuum (i.e. pressure less than the pressure of the external environment) in the cavity once the rubber wall is allowed to assume its original shape. This temporary vacuum is used to draw the mucus from the nasal passage. The problems associated with a manual bulb syringe are that suction is only imparted for a short time and the bulb syringe has to be inserted and removed from the nasal passage each time the partial vacuum is to be created, which is irritating for the child, moreover, there is no control over the degree of suction. These problems are overcome by providing the collection member with external means for imparting a suction action to the collection member for sucking mucus from the nasal passages. According to FR 98 03092 the partial vacuum is created by manually sucking at a hose connected to the collection member. According to utility model HU 3471 and HU 3472 the collection member may be connected to the hose of a vacuum cleaner. According to U.S. Pat. No. 5,800,425 a special purpose motor propelling a suction wheel is connected to the collection member via a hose. The main problem associated with these type of nasal aspirators is that some of the mucus drawn into the collection member may enter the hose and eventually the source of the suction action. In case of manually sucking at the end of the hose this is unhygienic, likely to cause contamination not to mention the inconvenience for the user imparting the suction action. In case of using a vacuum cleaner or special purpose motor or similar vacuum producing device the mucus entering the device is difficult to clean (if at all possible) and can also damage the device causing failure or break-down. The common way of avoiding these type of problems is to apply a filter at the hose connection of the collection member or inside the hose, however, liquid mucus can still get past such filters, moreover the filter can get blocked by the mucus whereby the suction action is inhibited.

It is an object of the present invention to overcome the problems associated with the prior art. In particular, it is an object of the invention to provide a collection member having an inner structure that prevents both liquid and solid mucus from being drawn out of the collection member through a hose connection end thereof. It is a further object to ensure this function in any position of the collection member, for example even if it is held upside down. It is a further object to provide a collection member that is easy to assemble and disassemble for cleaning purposes.

The above objects are achieved by a collection member according to the appended claims.

Further advantageous embodiments of the invention are defined in the attached dependent claims.

Further details of the invention will be apparent from the accompanying figures and exemplary embodiments.

FIG. 1 is a side view of a preferred embodiment of a collection member according to the invention.

FIG. 2 is a sectional view of the collection member taken along line A-A of FIG. 1.

FIG. 3 is a sectional view of the collection member according to FIG. 1 taken along line B-B of FIG. 2.

FIG. 4 is a sectional view of the collection member according to FIG. 1 taken along line C-C of FIG. 3.

Figure 6:
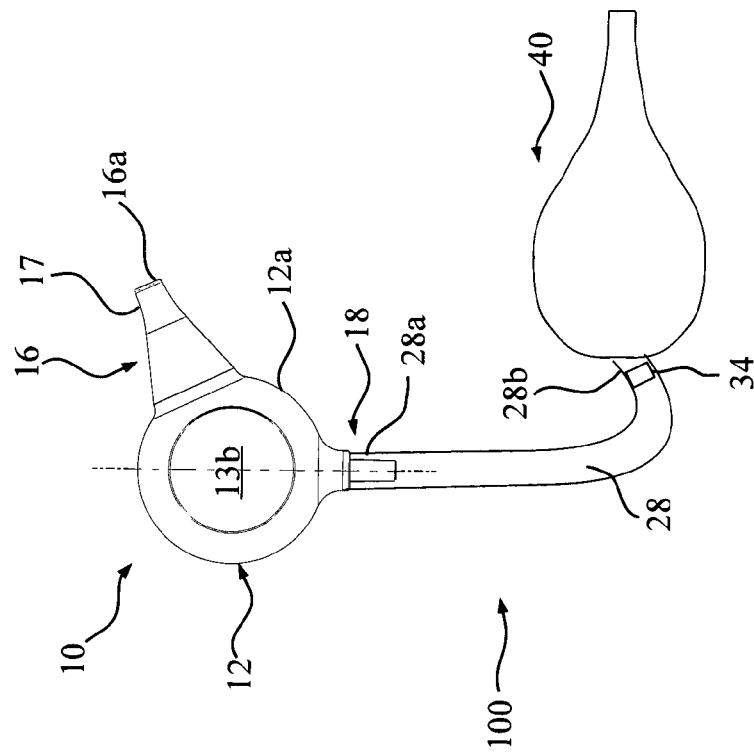
FIG. 6 is a schematic side view of another embodiment of a nasal aspirator comprising the collection member according to FIG. 1.

FIGS. 1 to 4 illustrate a preferred embodiment of a collection member 10 for a nasal aspirator in accordance with the present invention. The collection member 10 has a shell 12 defining an inner cavity 14. The shell 12 is provided with a nasal insertion end 16 for insertion into the nasal passage of a passive user (typically a young child or weak or disabled person as opposed to the active user holding and operating the collection member 10) and a hose connection end 18 for receiving a hose (not shown) that connects the collection member 10 with a source for imparting suction action and having an outlet 18a for allowing air to be drawn from the collection member 10 through the hose.

The nasal insertion end 16 preferably comprises a tapered wall having a proximal end 17 wherein an inlet 16a is provided for drawing in mucus from the nasal passage of the passive user. The nasal insertion end 16, and in particular its proximal end 17 are preferably tapered so as to be easily insertable into the nasal passage of the passive user. To further facilitate insertion of the nasal insertion end 16 it is preferably made of a soft, deformable material such as silicon or thermoplastic elastomers (TPE), such as the Thermoflex products of Plastic Technology Service Ltd. (UK). Suitable deformable materials may have a Shore hardness of 30 to 70, an elasticity (elastic modulus) of 35 to 50%, preferably about 43%, and a disruptive strength of 10 to 25 kN/m, preferably about 18 to 19 kN/m. The outer perimeter of the nasal insertion end 16 and in particular, the proximal end 17 may be dimensioned in accordance with the targeted passive user group, i.e. smaller nasal insertion end 16 may be provided for babies and young children, and greater nasal insertion end 16 for e.g. disabled adult passive users.

A first tubular element 20 is provided inside the collection member 10, which protrudes from the nasal insertion end 16 into the inner cavity 14 of the shell 12 whereby a first inner end 21 of the first tubular element 20 is located inside the inner cavity 14. The first tubular element 20 is arranged such that it provides a passage between the inlet 16a of the nasal insertion end 16 and the inner cavity 14 of the shell 12. This allows for drawing in mucus through the inlet 16a of the nasal insertion end 16 into the inner cavity 14 of the collection member 10.

The first tubular element 20 may be formed integrally with the nasal insertion end 16.

A second tubular element 22 is also provided inside the collection member 10, which protrudes from the hose connection end 18 into the inner cavity 14 whereby a second inner end 23 of the second tubular element 22 is located in the cavity 14 of the shell 12. The second tubular element 22 is arranged such that it provides a passage between the outlet 18a of the hose connection end 18 and the inner cavity 14 of the shell 12. This allows for sucking out air from the inner cavity 14 of the collection member 10 through the outlet 18a of the hose connection end 18.

A collar 24 is provided around the second tubular element 22 such that it is interposed between the first inner end 21 of the first tubular element 20 and the second inner end 23 of the second tubular element 22. By separating the first inner end 21 of the first tubular element 20 where the mucus enters the cavity 14 of the collection member 10 and the second inner end 23 of the second tubular element 22 through which the air is sucked out from the cavity 14, the mucus cannot directly enter the second inner end 23 and be thus drawn into the hose and eventually into the source of the suction action (or block any interposed filters). The collar 24 further serves to prevent mucus from climbing up the outer wall 22a of the second tubular element 22 as a result of the suction action exerted through the second inner end 23, whereby the mucus could eventually reach the second inner end 23 and be drawn into the second tubular element 22 there through. The inner design and dimensions of the collection member 10 preferably further contribute to preventing mucus from entering the second tubular element 22.

The collar 24 is preferably provided in the vicinity of the second inner end 23 for example such that the collar 24 is connected to the second tubular element 22 at a distance to the second inner end, which distance is about 1 to 10 mm, more preferably 1 to 5 mm, most preferably 1.5 to 3 mm. The spacing between the collar 24 and the second inner end 23 serves as a further obstacle that prevents mucus from entering the second inner end 23 should the mucus somehow get on the side of the collar 24 facing the second inner end 23 (e.g. if the collection member 10 is turned upside down, and then back again).

The collar 24 preferably comprises a convex wall 24a that opens in the direction of the second inner end 23, i.e. the collar 24 is at least partly cup shaped and faces the second inner end 23. The convex (cup shaped) wall 24a opening in the direction of the second inner end 23 further helps to keep the mucus out of the second tubular element 22. For example when the collection member 10 is held in the upside down position (with the hose connection end 18 being at its top) in which case the mucus drawn in through the first tubular element 20 is projected onto the outer wall 22a of the second tubular element 22 and runs down in the direction of the second inner end 23. In this situation the cup shaped wall 24a of the collar 24 conducts the mucus away from the second inner end 23.

The convex wall 24a of the collar 24 may have an inner radius of curvature R1 between 16 to 20 mm, preferably between 18 to 19.5 mm, being most preferably about 18.8 mm, and the convex wall 24a of the collar 24 may have an outer radius of curvature R2 between 17 to 21 mm, preferably between 19 to 20.5 mm, being most preferably about 19.8 mm.

The wall 24a of the collar 24 may have other shapes as well. For example the wall 24a of the collar 24 may be substantially conical, elliptic, paraboloid or hyperboloid, or it may have any other—even irregular—shape which is at least partly convex in the sense that it defines a cup shaped space that opens in the direction of the second inner end 23.

The collar 24 preferably terminates in a circular or oval edge 24b. Furthermore, the edge 24b is preferably substantially level with the second inner end 23, however the second tubular element 22 may be designed such that the second inner end 23 extends from the cup shaped space defined by the wall 24a of the collar 24 or such that the second inner end 23 is located within this space.

The first tubular element 20 and the second tubular element 22 are preferably arranged such that the axis $t_1$ of the first tubular element 20 traverses the axis $t_2$ of the second tubular element 22 and the angle α formed by the two axes $t_1$, $t_2$ is between 25° to 90°, preferably 45° to 80°, more preferably 60° to 70°, being most preferably about 65°. This arrangement has proven to render the best hydrodynamic performance. It has been found that liquid mucus is best prevented from being pulverised if it hits the second tubular element 22 at this preferred angle. Pulverisation of the mucus should be avoided as the pulverised particles start to circulate within the cavity 14 of the collection member 10 and may be thus drawn into the second tubular element 20 together with the air in spite of the collar 24 provided thereon. In order to ensure the desired angle the axis $t_1$ of the first tubular element 20 may coincide or deviate from the axis of the nasal insertion end 16.

The shell 12 preferably comprises two grabbing areas 13a and 13b on opposite sides of the shell 12. These grabbing areas 13a and 13b are preferably designed ergonomically for allowing easy holding of the shell 12 of the collection member 10. For example the shell 12 may be formed as a sphere such that the shape of the shell 12 deviates from the spherical shape at the two grabbing areas 13a, 13b in order to facilitate holding of the shell 12. For example the two grabbing areas 13a, 13b may be formed as substantially flat surfaces. In the context of the present invention a substantially flat surface indicates a surface that does not deviate from a flat plane by more than +/−10 mm, and preferably not more than +/−5 mm. For example the substantially flat grabbing areas 13a, 13b may be slightly indented (as shown in FIG. 4) or ribbed for more secure grabbing, or provided with a logo or other visible mark e.g. in the form of an embossment 13c.

The nasal insertion end 16, the hose connection end 18 and the grabbing areas 13a, 13b are preferably located such that the nasal insertion end 16 and the hose connection end 18 define a common plane of symmetry and the grabbing areas 13a, 13b are located symmetrically with respect to this common plane of symmetry. For example the nasal insertion end 16 and the hose connection end 18 are located along a spherical perimeter 12a between the two grabbing areas 13a, 13b.

Preferably the second tubular element 22 traverses the centre of the shell 12 and the first inner end 21 of the first tubular element 20 faces the centre of the shell 12. In case of the substantially spherical shell 12 with optional grabbing areas 13a, 13b, the centre of the shell 12 is the centre of the sphere (practically the centre defined by the spherical enveloping surface). However, a geometric centre for the cavity 14 serving to collect mucus can be defined even in case the shape of the shell 12 is not spherical.

The collar 24 is preferably spaced apart from the portion of the shell 12 facing the collar 24. Preferably the collar 24 is dimensioned and positioned such that regardless of the position of the collection member 10 (e.g. being held upside down when its hose connection end 18 is at its top, or being tilted side ways when one of the grabbing areas 13a, 13b is at its top) the collar 24 does not reach the mucus deposited on the inner side of the shell 12 (having regard to the usual amount of mucus collected during one use), hence the mucus cannot creep up along the wall 24a of the collar 24 and eventually the wall 22a of the second tubular element 22 and be drawn into the second tubular element 22 through the second inner end 23.

For this reason the distance between the edge 24b of the collar 24 and the inner side of the grabbing areas 13a, 13b of the shell 12 is preferably between 5 to 15 mm, preferably 7 to 13 mm, being more preferably 8 to 10 mm.

In order to prevent mucus from being drawn into the second tubular element 22 when the collection member 10 is held in the upside down position, the distance between the second inner end 23 of the second tubular element 22 and the portion of the shell 12 facing the second inner end 23 is preferably at least 10 mm, preferably between 13 to 20 mm, more preferably 14 to 18 mm, most preferably 15 to 16 mm.

In order to achieve good hydrodynamic and aerodynamic properties, the inner diameter $d_1$ of the first tubular element 20 is between 3 to 6.5 mm, preferably 3.5 to 6 mm. According to a particularly advantageous embodiment the first tubular element 20 has a varying inner diameter $d_1$ along its length that starts with a diameter $d_1$ falling between 3 to 6.5 mm, being preferably about 3.9 mm at the inlet 16a of the nasal insertion end 16, and terminates at the first inner end 21 in a diameter $d_1$ falling between 4 to 6 mm, being preferably about 5.5 mm.

In order to achieve good aerodynamic properties, the inner diameter $d_2$ of the second tubular element 22 at its second inner end 23 is preferably between 2.5 to 8 mm, preferably 3 to 7 mm, being most preferably about 6.8 mm. The inner diameter $d_2$ of the second tubular element 22 may be constant or it may vary along its length.

Preferably the collection member 10 can be disassembled in order to facilitate cleaning thereof. The shell 12 is preferably made up more than one parts, preferably of two parts (halves) that can be taken apart and connected again. The connection is preferably form fitting (as shown in FIGS. 2 and 4) or screw connection or any other known type of connection that provides substantially hermetic sealing of the inner cavity 14 in order to maintain the low pressure inside the collection member 10 during use. Disassembling preferably includes the possibility of removing the nasal insertion end 16 preferably together with the first tubular element 20, and the possibility of removing the second tubular element 22 from the hose connection end 18, wherein any kind of sealing connection 19 may be provided for receiving and holding the second tubular element 22.

Figure 5:
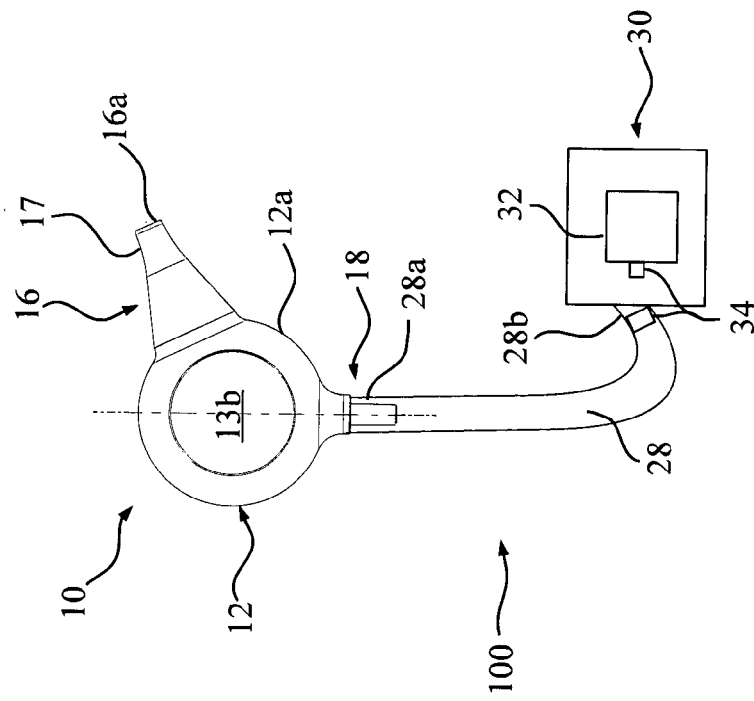
FIG. 5 is a schematic side view of a nasal aspirator comprising the collection member according to FIG. 1.

FIG. 5 illustrates a nasal aspirator 100 according to the invention comprising the collection member 10 depicted in FIG. 1. The nasal aspirator 100 comprises a hose 28, a first end 28a of which is connected to the hose connection end 18 of the collection member 10. The nasal aspirator 100 further comprises a schematically illustrated motor assembly 30 connected to a second end 28b of the hose 28, for imparting suction action through the hose 28. The motor assembly 30 preferably includes a suction motor 32 suitable of creating partial vacuum in the collection member 10 by sucking air therefrom through the hose 28. The suction motor 32 preferably has a variable power output between 100-600 W, more preferably between 200-400 W and a vacuum of 100-130 mbar (100-130 hPa).

Preferably a filter 34 is applied either in the motor assembly 30 or in the hose 28 in order to protect the suction motor 32 from any mucus that is somehow drawn into the hose 28, in particularly in case of improper use (for example the second tubular element 22 is left out when reassembling the collection member 10 after cleaning).

According to another possible embodiment the motor assembly 30 is a common vacuum cleaner as described in Hungarian utility models HU 3471 and HU 3472.

According to a further possible embodiment the second end 28b of the hose 28 is connected to a mouth piece 40 for manually sucking by mouth air from the collection member 10 and thereby creating a partial vacuum therein.

The nasal aspirator 100 according to the invention is operated as follows. The active user inserts the proximal end 17 of the nasal insertion end 16 of the collection member 10 into the nasal passage of the passive user, whereby the inlet 16a of the nasal insertion end 16 is located inside the nasal passage. After this suction action is imparted to the cavity 14 of the collection member 10 via the hose 28 connected to the hose connection end 18. For example in case of the embodiment disclosed in FIG. 6 the suction action is imparted manually such that the active user sucks air out of the cavity 14 of the collection member by sucking the mouth piece 40. In case of the embodiment depicted in FIG. 5 the suction action is imparted by activating the motor assembly 30 connected to the hose 28. As a result of the suction action partial vacuum is created in the cavity 14 of the collection member 10 and thus inside the first tubular element 20 sucking the mucus out of the passive user's nasal passage through the inlet 16a of the nasal insertion end 16.

Various modifications to the above disclosed embodiments will be apparent to a person skilled in the art without departing from the scope of protection determined by the attached claims.

The invention claimed is:

1. Collection member (10) for a nasal aspirator (100), the collection member (10) having a shell (12) defining a cavity (14), which shell (12) is provided with a nasal insertion end (16) and a hose connection end (18), and comprising:
   a first tubular element (20) protruding from the nasal insertion end (16) into the cavity (14) such that a first open inner end (21) of the first tubular element (20) is located in the cavity (14),
   a second tubular element (22) protruding from the hose connection end (18) into the cavity (14) such that a second open inner end (23) of the second tubular element (22) is located in the cavity (14),
   a collar (24) on an outer wall (22a) of the second tubular element (22), surrounding the second open inner end, spaced from the second open inner end, and terminating in a circular edge (24b),
   and the first and second tubular elements (20, 22) are arranged such that the collar (24) is interposed between the first open inner end (21) and the second open inner end (23),
   the axis ($t_i$) of the first tubular element (20) traversing the axis ($t_2$) of the second tubular element (22), wherein the angle ($\alpha$) formed by the two axes ($t_i$, $t_2$) is between 25° to 90°, and the first tubular element extends beyond the edge 24(b) of the collar (24).

2. The collection member according to claim 1, characterised by that the collar (24) comprises an at least partly convex wall (24a) that opens in the direction of the second open inner end (23).

3. The collection member according to claim 2, characterised by that the at least partly convex wall (24a) has an inner radius of curvature (R1) between 16 to 20 mm, and the wall (24a) has an outer radius of curvature (R2) between 17 to 21 mm.

4. The collection member according to claim 1, characterised by that the edge (24b) which is level with the second inner end (23).

5. The collection member according to claim 1, characterised by that the shell (12) comprises two defined grabbing areas (13a, 13b) on opposite sides of the shell (12).

6. The collection member according to claim 5, characterised by that the shell (12) is formed as a sphere and the shape of the shell (12) deviates from the spherical shape at the two grabbing areas (13a, 13b).

7. The collection member according to claim 5, characterised by that the nasal insertion end (16) and the hose connection end (18) are located along a spherical perimeter between the two grabbing areas (13a, 13b).

8. The collection member according to claim 5, characterised by that the distance between the edge (24b) of the collar (24) and the inner side of the grabbing area (13a, 13b) of the shell (12) is between 5 to 15 mm.

9. The collection member according to claim 1, characterised by that the distance between the second inner end (23) of the second tubular element (22) and the portion of the shell (12) facing the second inner end (23) is between 13 to 20 mm.

10. The collection member according to claim 1, characterised by that the second tubular element (22) traverses the centre of the shell (12) and the first inner end (21) of the first tubular element (20) faces the centre of the shell (12).

11. The collection member according to claim 1, characterised by that the second tubular element (22) is removably attached to the shell (12) at the hose connection end (18).

12. The collection member according to claim 1, characterised by that the nasal insertion end (16) comprises a tapered wall having a proximal end (17), wherein an inlet (16a) is provided, and the first tubular element (20) is provided such that it connects the inlet (16a) with the cavity (14) of the shell (12).

13. The collection member according to claim 1, characterised by that the nasal insertion end (16) and the first tubular element (20) are integral.

14. The collection member according to claim 1, characterised by that the inner diameter ($d_1$) of the first tubular element (20) is between 3 to 6.5 mm.

15. The collection member according to claim 1, characterised by that the inner diameter ($d_2$) of the second tubular element (22) at its second inner end (23) is between 2.5 to 8 mm.

16. The collection member according to claim 1, further comprising a hose (28) having a first end (28a) and a second end (28b), the first end (28a) of which is connected to the hose connection end (18), and a motor assembly (30) connected to the second end (28b) of the hose (28), for imparting suction action through the hose (28).

17. The collection member according to claim 1, characterised by comprising a hose (28) having a first end (28a) and a second end (28b), the first end (28a) of which is connected to the hose connection end (18), and comprising a mouth piece (40) connected to the second end (28b) of the hose (28), for manually imparting suction action through the hose (28).

* * * * *

UNITED STATES PATENT AND TRADEMARK OFFICE
CERTIFICATE OF CORRECTION

| | |
|---|---|
| PATENT NO. | : 9,649,414 B2 |
| APPLICATION NO. | : 14/765371 |
| DATED | : May 16, 2017 |
| INVENTOR(S) | : Valter Streitmann et al. |

It is certified that error appears in the above-identified patent and that said Letters Patent is hereby corrected as shown below:

In the Claims

Column 6,
Line 51, "$(t_i)$" should be -- $(t_1)$ --.
Line 53, "$(t_i, t_2)$" should be -- $(t_1, t_2)$ --.
Line 66, after "(24b)" delete "which".

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*